United States Patent [19]

Richter et al.

[11] Patent Number: 5,336,500

[45] Date of Patent: Aug. 9, 1994

[54] SANITIZING COMPOSITION COMPRISING A BLEND OF AROMATIC AND POLYUNSATURATED CARBOXYLIC ACID

[75] Inventors: Francis L. Richter, Circle Pines; Daniel E. Pedersen, Cottage Grove; May J. Biedscheid, St. Paul; Dale L. Fredell, Lindstrom, all of Minn.

[73] Assignee: Ecolab Inc., St. Paul, Minn.

[21] Appl. No.: 989,506

[22] Filed: Dec. 11, 1992

Related U.S. Application Data

[63] Continuation of Ser. No. 710,095, Jun. 4, 1991, abandoned.

[51] Int. Cl.$^5$ .................. A01N 25/02; A01N 37/06
[52] U.S. Cl. .................................... 424/405; 422/28
[58] Field of Search .................. 424/404, 405, 409; 514/557, 558, 576; 422/28

[56] References Cited

U.S. PATENT DOCUMENTS

| | | | |
|---|---|---|---|
| 2,466,663 | 4/1949 | Russ et al. | 167/58 |
| 3,650,965 | 3/1972 | Cantor et al. | 252/106 |
| 3,867,300 | 2/1975 | Karabinos | 252/106 |
| 3,915,633 | 10/1975 | Ramachandran | 8/137 |
| 4,002,775 | 1/1977 | Kabara | 426/532 |
| 4,376,787 | 3/1983 | Lentsch et al. | 424/315 |
| 4,404,040 | 9/1983 | Wang | 134/22.14 |
| 4,406,884 | 9/1983 | Fawzi et al. | 424/81 |
| 4,410,442 | 10/1983 | Lucas et al. | 252/107 |

(List continued on next page.)

FOREIGN PATENT DOCUMENTS

| | | |
|---|---|---|
| 0021504 | 1/1981 | European Pat. Off. |
| 0068552 | 1/1983 | European Pat. Off. |
| 0083820 | 7/1983 | European Pat. Off. |
| 0097995 | 1/1984 | European Pat. Off. |
| 0147102 | 7/1985 | European Pat. Off. |
| 0244144 | 1/1987 | European Pat. Off. |
| 0218441 | 4/1987 | European Pat. Off. |
| 0245928 | 11/1987 | European Pat. Off. |

(List continued on next page.)

OTHER PUBLICATIONS

Food Acidulants, pp. 7, 13, 44 and Chapter 8, pp. 97–114.

Kirk–Othmer Encyclopedia of Chemical Technology, Third Edition: Dicarboxylic Acids, vol. 7, pp. 614–628; Carbonated Beverages, vol. 4, pp. 712–713; Citric Acid, vol. 6, pp. 150–179; Hydroxy Carboxylic Acids, vol. 13, pp. 80–121; and Carboxylic Acids, vol. 4, pp. 814–871.

PCT International Search Report (PCT/US92/00794).

(List continued on next page.)

*Primary Examiner*—Thurman K. Page
*Assistant Examiner*—Neil Levy
*Attorney, Agent, or Firm*—Merchant, Gould, Smith, Edell, Welter & Schmidt

[57] ABSTRACT

The invention generally comprises a composition capable of sanitizing and disinfecting antimicrobial efficacy while also being ingestible as a food additive residue by humans and mammals. Specifically, the microbicidal composition of the invention generally comprises a carrier and an antimicrobial agent, wherein the antimicrobial agent generally comprises a $C_5$ to $C_4$ unsaturated monocarboxylic acid such as sorbic acid, in combination with an aromatic carboxylic acid such as benzoic acid. The antimicrobial composition of the invention is useful for both hard and soft surface sanitizing in environments such as farms, milk and food processing, fluid milk operations, institutional food preparation and serving areas, health care and child care facilities, as well as any other number of contact sensitive environments which require compositions having high antimicrobial efficacy and which will not contaminate food stocks and which pose no danger to humans. Also disclosed are concentrate and solid compositions stemming from the invention as well as the method of using the composition of the invention in sanitizing and disinfecting applications.

1 Claim, 1 Drawing Sheet

U.S. PATENT DOCUMENTS

| | | | |
|---|---|---|---|
| 4,430,381 | 2/1984 | Harvey et al. | 428/284 |
| 4,647,458 | 3/1987 | Ueno et al. | 424/128 |
| 4,715,980 | 12/1987 | Lopes et al. | 252/106 |
| 4,776,974 | 10/1988 | Stanton et al. | 252/106 |
| 4,920,100 | 4/1990 | Lehmann et al. | 514/23 |
| 4,945,110 | 7/1990 | Brokken et al. | 514/517 |
| 5,013,560 | 5/1991 | Stentz et al. | 424/653 |
| 5,017,617 | 5/1991 | Kihara et al. | 514/635 |

FOREIGN PATENT DOCUMENTS

| | | |
|---|---|---|
| 0288689 | 11/1988 | European Pat. Off. |
| 0375827 | 7/1990 | European Pat. Off. |
| 1937682 | 1/1970 | Fed. Rep. of Germany. |
| 2122284 | 9/1972 | France. |
| 2233049 | 10/1974 | France. |
| 59-157007 | 9/1984 | Japan. |
| 62-048612 | 3/1987 | Japan. |
| WO83/00163 | 1/1983 | PCT Int'l Appl. |
| WO91/05842 | 5/1991 | PCT Int'l Appl. |
| 1595431 | 9/1990 | U.S.S.R. |
| 2103089A | 6/1987 | United Kingdom. |
| 2211093 | 6/1989 | United Kingdom. |

OTHER PUBLICATIONS

Seymour S. Block, Disinfection, Sterilization, and Preservation, Fourth Edition, 1991, Chapter 47, "Chemical Food Preservatives".

Seymour S. Block, Disinfection, Sterilization, and Preservation, Second Edition, 1977, Chapter 16, "Acid-Anionic Surfactant Sanitizers".

Code of Federal Regulations, 21 C.F.R. Ch. 1 (Apr. 1, 1991 Edition), pp. 311–318.

Kirk-Othmer, Encyclopedia of Chemical Technology, Third Edition, vol. 12, pp. 46, 61 and 62.

The Food Chemical News Guide, Oct. 7, 1991.

The Food Chemical News Guide, Jun. 26, 1989.

Clinical Toxicology of Commercial Products, Fifth Edition, 1984.

Whistler, Industrial Gums.

Food and Science and Technology, pp. 186 and 187.

Chemical Abstracts, Abstract No. 95723, vol. 111, p. 610, (1989).

Committee on Specification . . ., *Food Chemical Codex*, Second Edition, pp. 12–14.

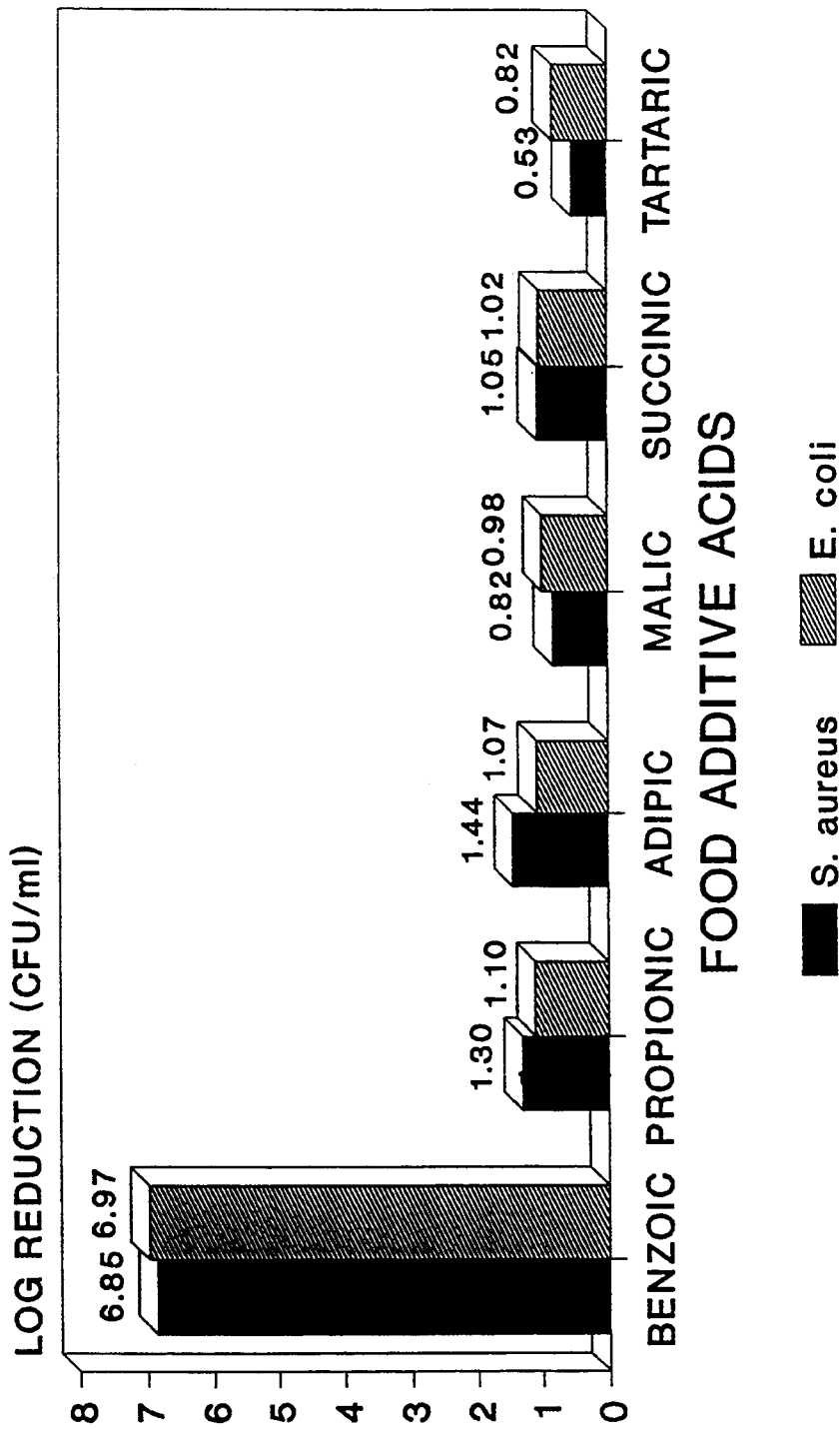

SANITIZING COMPOSITION COMPRISING A BLEND OF AROMATIC AND POLYUNSATURATED CARBOXYLIC ACID

This is a continuation of application Ser. No. 07/710,095, filed Jun. 4, 1991, which is now abandoned.

FIELD OF THE INVENTION

The invention relates to microbicidal compositions for sanitizing food contact surfaces and for disinfecting critical day-care and health-care environments. More specifically, the present invention relates to food additive microbicidal compositions which include carboxylic acid antimicrobial agents and which are preferably safe for incidental human contact, as well as food contact surfaces without requiring a post sanitizing rinse. The microbicidal compositions of the invention are suitable for food process plants, food preparation kitchens, food serving establishments, child-care and nursing-care and hospital-care applications, as well as for domestic households where concern exists for human contact or ingestion and safety of environmental residues.

BACKGROUND OF THE INVENTION

The list of approved antimicrobial agents has decreased due to their human toxicity and their detrimental effect on water supplies and the environment. Improving analytical capabilities to detect parts-per-billion levels in food, water and in the environment, has raised important safety concerns about the application and misapplication of these chemicals. These issues have resulted in the banning of some antimicrobials, for example hexachlorophene; the retesting of others for animal toxicity, such as, the quaternary ammonium compounds; and, increasing scrutiny of species such as chlorine or hypochlorites which may form toxic halocarbons in effluent waters.

There has been a long felt need for antimicrobial agents which have a high degree of antimicrobial efficacy, and which are preferably safely ingestible by humans while posing no environmental incompatibility. Those antimicrobial agents which are lethal to microorganisms, however, are also toxic in varying degrees to humans and animals in that both higher and lower forms of life share at least some metabolic pathways. Competitive inhibition, non-competitive inhibition, protein coagulation, oxidative and reductive action, blockage of enzyme systems are thought to be some of the mechanisms involved in the destruction of microorganisms. Differentiation of antimicrobial "-cidal" or "-static" activity, the definitions which describe the degree of efficacy, and the official laboratory protocols for measuring this efficacy are important considerations for understanding the relevance of antimicrobial agents and compositions. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed microbicidal and the latter, bacteriostatic. A sanitizer and a disinfectant are, by definition, agents which provide microbicidal activity. In contrast, a preservative is generally described as inhibitory or bacteriostatic.

A sanitizer is an agent that reduces the number of bacterial contaminants to safe levels as judged by public health requirements. Practically, a sanitizer must result in 99.999% reduction (5 log order reduction) for given organisms as defined by *Germicidal and Detergent Sanitizing Action of Disinfectants,* Official Methods of Analysis of the Association of Official Analytical Chemists, paragraph 960.09 and applicable sections, 15th Edition, 1990 (EPA Guideline 91-2). In common practice, substances that are applied to food contact surfaces for antimicrobial purposes must meet this requirement.

A disinfectant is an agent that kills all vegetative cells including most recognized pathogenic microorganisms. As such, it must pass a more stringent antimicrobial test; the *A.O.A.C. Use Dilution Methods.,* Official Methods of Analysis of the Association of Official Analytical Chemists, paragraph 955.14 and applicable sections, 15th Edition, 1990 (EPA Guideline 91-2).

In contrast, a preservative is described as any agent that extends the storage life of food and non-food products by retarding or preventing deterioration of flavor, odor, color, texture, appearance, nutritive value, or safety. The criteria used for evaluating such materials is designated Minimum Inhibitory Concentration. Another procedure is entitled Zone of Inhibition. Preservatives, by definition, are therefore inhibitory substances added to food to prolong or enhance shelf-life. The principal differences between a preservative and a sanitizer are two-fold: 1) mode of action—a preservative prevents growth rather than killing microorganisms like a sanitizer; and, 2) exposure time—a preservative has days to months. In contrast, a sanitizer must provide 99.999% kill (5 log order) within 30 seconds at nominal 20° C.

Ideally, a sanitizing agent or compound will possess several important properties in addition to its antimicrobial efficacy. The sanitizer should be no-rinse after application, and exhibit residual antimicrobial activity. Residual activity means a film of sanitizing material which will continue to have antimicrobial effect if the treated surface is contaminated by microorganisms during a storage or lag period. The sanitizer should preferably be composed of direct food additive materials which will not affect food if contact occurs, nor affect humans should incidental ingestion result. The sanitizer should be odor free to prevent transfer of undesirable odors onto foodstuffs.

Previously, certain compositions have been recognized as effective in maintaining the condition of food products. For example, U.S. Pat. No. 4,404,040 to Wang discloses the sanitizing properties of short chain fatty acids formulated with an ionic hydrotrope-solubilizer and compatible acids. However, Wang does not focus on the antimicrobial efficacy of unsaturated alkyl-/aromatic carboxylic acid combinations nor the efficacy of these compounds when used with certain adjuvants.

U.S. Pat. No. 4,647,458 to Ueno et al, discloses bactericidal compositions comprising a large portion of ethyl alcohol, an organic acid, and an inorganic acid. However Ueno's disclosure is also not specific to sorbic/benzoic acid systems.

U.S. Pat. No. 3,915,633 to Ramachandran, discloses a prewash composition for treating fabrics which includes an organic acid such as citric acid and either a nonionic or an anionic surfactant.

U.S. Pat. No. 3,867,300 to Karabinos, discloses bactericidal compositions presumably for controlling the spread of nosocomial infections in hospitals consisting of an aliphatic monocarboxylic acids, and nonionic surfactants. U.K. Patent Application GB 2,103,089A to Kimberly Clark, discloses the use of carboxylic acids as virucides. U.S. Pat. No. 4,715,980 to Lopes et al, discloses an antimicrobial concentrate composition containing a dicarboxylic acid, a solubilizer, an acid and a diluent. U.S. Pat. No. 3,650,965 to Cantor et al, discloses clean-in-place detergent solutions for treating milk and food processing equipment based on two different nonionic surfactants.

U.S. Pat. No 4,002,775 to Kabara discloses the use of mono-esters of twelve carbon aliphatic fatty acid and polyols. European Patent Application No. 87303488 to Kabara discloses antimicrobial preservative compositions of glycerol mono esters.

However similar to Wang and Ueno et al, the disclosure in these publications is not specific to sorbic-benzoic acid compositions and further does not disclose the antimicrobial activity of these acids in conjunction with their use with certain adjuvants.

Currently, products used for sanitizing operations include strong oxidizing agents such as peracetic acid, iodophors, sodium hypochlorite, and related n-chloro compounds such as chloro isocyanurates, quaternary ammonium compounds, acid compositions containing dodecyl benzene sulfonic acid or carboxylic acid and the like. While these are no rinse sanitizers, they are not ideal for one reason or another.

Peracetic acid, iodophors and chlorine based sanitizers are either decomposed or lost by evaporation when a film of sanitizer is left on food contact surface and allowed to dry. Thus no residual activity remains on the intended surface. Residual activity is necessary to provide continued antimicrobial effect if the surface is contaminated by microorganisms during storage.

Quaternary ammonium compounds (QAC) have excellent residual property as they are stable and increase in concentration as the solvent (water) evaporates. Unfortunately, for other uses, this residue may be carried over into the food product. In fact, even a trace of the QAC in milk inhibits the starter culture which produces lactic acid and flavor resulting in the curdling of milk protein.

Acid based sanitizers often contain surfactant couplers which are not food additive. Moreover, certain carboxylic acid based sanitizers have undesirable organoleptic properties such as a "goat-like" rancid odor. Moreover, longer chain fatty acids have limited solubilities in water and require thorough rinsing with potable water before contact of the sanitized surface with food stuff to avoid imparting off-flavor to the food.

While all these compositions are excellent sanitizers, many of their ingredients are not food additive. Consequently, these current, commercially successful products have not been designed for user safety, potential misapplication or environmental compatibility. Thus a sanitizing agent which specifically addresses these issues would possess utility and uniqueness not found in heretofore described sanitizers.

SUMMARY OF THE INVENTION

The invention is based on the surprising discovery of a antimicrobial composition composed of food additive ingredients capable of providing sanitizing and, in fact, disinfecting antimicrobial efficacy. The composition comprises a carrier and an antimicrobial agent, with the agent comprising a $C_{5-14}$ di-unsaturated monocarboxylic acid or salts thereof and an aromatic carboxylic acid or salts thereof comprising the formula

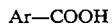

wherein Ar comprises an aromatic structure such as a benzene structure.

The invention also includes a food additive antimicrobial concentrate comprising a carrier and a similar antimicrobial agent as well as a method of sanitizing soft or hard surfaces preferably using a food additive antimicrobial composition of the invention. Optionally, the present invention may also contain a variety of formulary or application adjuvants.

The composition of the invention eliminates the potential for recontamination of sanitized surfaces by eliminating the need for a potable water rinse which may be safe to drink but may contain food spoilage bacteria. This is particularly important when there is a delay between sanitizing operation and use of the equipment. In cases where equipment remains wet between uses, contaminating organisms may grow freely.

Airborne contamination may also be prevented by the invention by retention on surfaces. Especially in the presence of moisture, residue resulting from the composition of the invention will continue its antimicrobial action. When residual amounts of the invention are retained on the surface of application, continued sanitizing action will occur in the face of exposure to contamination.

The invention is also applicable to closed systems such as pipelines and holding tanks which are difficult to completely drain. When used, the invention will continue to effectively destroy any microorganisms which might be present in pipelines or holding tanks without creating the risk of harmful food contamination or environmental contamination.

BRIEF DESCRIPTION OF THE FIGURE

The FIGURE comprises a graphical representation of the antimicrobial efficacy of the invention in comparison to other compositions as reported in Working Example I.

DETAILED DESCRIPTION OF THE INVENTION

The invention comprises a composition capable of imparting sanitizing and, in fact, disinfecting antimicrobial efficacy. In its most preferred form, the invention comprises an antimicrobial agent and a carrier which are approved as food additives. The composition may also comprise an acidulant along with any variety of other formulatory or application adjuvants.

This invention also comprises concentrate and use solution formulations which may take the form of liquid solutions, towelettes, gels, impregnated sponges, lotions, personal care cleansers, pump sprays, aerosol sprays, foams and solids, in addition to methods of sanitizing and disinfection utilizing the composition of the invention.

I. Antimicrobial Agent

The composition of the invention generally comprises a two part antimicrobial agent. This antimicrobial agent comprises both aromatic and aliphatic polyunsaturated carboxylic acids.

The invention is based on a discovery that certain carboxylic acids, when combined, surprisingly provide extraordinary sanitizing, if not disinfecting, antimicrobial efficacy. This discovery, is enhanced by the fact that both acids preferably meet food grade purity requirements, in accordance with the Food Chemicals Codex, published by Food Chemical News, and are recognized Food Additives by the United States Food and Drug Administration. The antimicrobial agent of the invention provides a food additive sanitizing composition suitable for use in environments which heretofore had to be sanitized with less desirable agents and processes.

Generally, the antimicrobial agent of the invention functions to sanitize or disinfect the intended surface of application. Moreover, the antimicrobial agent of the invention is preferably recognized as food additive which may intentionally be included into compositions which are ultimately ingested by humans.

Thus, the composition of the invention will not leave a residue which, upon contact with foodstuffs, will contaminate and preclude ingestion of the prepared food. Generally, the composition of the invention is applicable to all food preparation environments such as dairy and food processing, preparation and serving facilities as well as other contact sensitive areas such as day and child care facilities, health care facilities, and domestic households.

Thus, a sanitizer and disinfectant which is excellent microbicidally, may be composed entirely of food additive ingredients, does not require a post-sanitizer rinse, imparts no off-flavor or odor to food, possess residual activity, and minimize the potential for acute and chronic human toxicity and environmental contamination fulfills a need not currently met by presently available sanitizers.

Generally, the antimicrobial agent of the invention comprises a two part carboxylic acid system. Carboxylic acids are characterized by the presence of one or more carboxyl groups which generally have the structure:

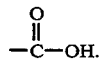

Carboxylic acids as a group are usually considered to be relatively weak acids. Most carboxylic acids are weaker than the weakest of the inorganic acids. However, we have found that two carboxylic acids, when used together, provide unique antimicrobial efficacy despite this classification.

Generally, the composition of the invention includes an antimicrobial agent having an aliphatic polyunsaturated carboxylic acid and an aromatic carboxylic acid including salts of these acids, and hydroxy derivatives of these acids, and esters of these acids.

Specifically, aliphatic carboxylic acids useful in the invention include poly-unsaturated monocarboxylic acids wherein their primary alkyl moiety comprises a carbon chain ranging in size from 5 to 12 carbon atoms.

Along with the polyunsaturated monocarboxylic acids useful in the invention, are carboxylic acid derivatives including carboxylic acid esters, or carboxylic acid salt derivatives.

Generally, the alkyl polyunsaturated monocarboxylic acid of the invention may take the form of a salt formed by reaction with an alkaline substance most commonly from oxides, hydroxides or carbonates of monovalent and divalent metals in Periodic Groups IA and IIA; but also with basic positive complexes such as ammonium radical and organic amine moieties. Preferably, these acid salts will be food additive so as to not contaminate finished foodstuffs through contact with food preparation surfaces.

The alkyl polyunsaturated monocarboxylic acid of the invention may also be derivatized as an ester. Common ester derivatives of polyunsaturated carboxylic acids useful in this invention include those wherein the hydroxy group is replaced by an alkoxy group which may also comprise any number of alkyl moieties which do not impeded the efficacy of the polyunsaturated monocarboxylic acid ester compound.

More preferably, the aliphatic carboxylic acids are di-unsaturated having an alkyl carbon chain which ranges in size from 5 to 8 carbon atoms. Most preferably the alkyl di-unsaturated monocarboxylic acid comprises sorbic acid as well as sorbic acid salts.

Generally, depending on whether the composition is a concentrate or use dilution formulation, the aliphatic poly-unsaturated carboxylic acids of the invention may be used in a concentration ranging generally from about 0.05 wt-% to about 80 wt-%, preferably from about 0.1 wt-% to about 70.0 wt-%, and most preferably from about 0.2 wt-% to about 60 wt-%.

The second element of the antimicrobial agent of the invention is an aromatic carboxylic acid. The aromatic carboxylic acid useful in the invention may be substituted or unsubstituted, as well as derivatized to form an hydroxy derivative ester, or salt of an aromatic carboxylic acid.

Generally, the aromatic carboxylic acid of the invention comprises a benzene ring structure which may be substituted or unsubstituted. Substitution will generally take the form of any number of moieties or compounds including dicarboxyl and anhydride species appended to the ring structure at any variety of locations.

The aromatic carboxylic acid of the invention may also be derivatized into the form of a carboxylic acid ester, or carboxylic acid salt.

Generally, the aromatic carboxylic acid of the invention may also take the form of a salt formed by reaction with an alkaline substance most commonly from oxides, hydroxides or carbonates of monovalent and divalent metals in Periodic Groups IA and IIA; but also with basic positive complexes such as the ammonium radical and organic amine moieties.

The aromatic carboxylic acid of the invention may also comprise an ester derivative of that carboxylic acid. Useful ester derivatives of carboxylic acids are those wherein the hydroxy group is replaced by an alkoxy group which may comprise any number of different alkyl or aryl moieties which do not impede the efficacy of the benzoic acid compound.

Accordingly, the aromatic carboxylic acid of the invention may comprise any number of acid salts, acid esters, as well as the substituted or unsubstituted aromatic acid compounds. For example, ethoxy benzoic acid, methoxy benzoic acid, benzoyl benzoic acid, hydroxy or dihydroxy benzoic acid as acid aldehydes and anhydrides and the like. Generally, aromatic carboxylic acids useful in the antimicrobial agent of the invention are those which contain at least one benzene ring structure and one or more carboxyl groups directly attached to the ring.

The composition of the invention preferably comprises food additive chemical compounds which will effectively, but safely, provide antimicrobial efficacy within the context of the invention. Preferably, the antimicrobial agent of the invention will comprise benzoic acid, salts of benzoic acid or esters of benzoic acid combinations thereof within the antimicrobial agent.

Generally, depending on whether the composition is a concentrate or use dilution formulation, the concentration of aromatic carboxylic acid useful in the invention in concentration ranges from about 0.05 wt-% to about 80 wt-% preferably from about 0.05 wt-% to 70 wt-%, and most preferably from about 0.05 wt-% to about 60 wt-%.

The concentration ranges for both the aromatic carboxylic acid and the alkyl polyunsaturated carboxylic acid are presented as guidelines. Actual concentrations vary depending upon the carrier used in the formulation, whether aqueous, organic, inorganic or a mixture thereof; and the overall nature of the formulation, whether neat solution, liquid concentrate, dispersion, emulsion, gel or solid; the delivery and application method; and the compositional adjustment necessary for physical and chemical stability during storage.

II. Carrier

The antimicrobial composition of the invention may also comprises a carrier. The carrier within this composition functions to dilute and transport the antimicrobial agents to the intended surface of application and define the form of the composition. Moreover, depending upon the nature of the carrier, this constituent may be used to maintain the antimicrobial agent on the intended surface for an extended period of time in the form of a film or food additive residue after application. Keeping these functions in mind, the carriers useful in the invention should preferably maintain the food additive character of the composition while not obscuring the efficacy of the antimicrobial agent.

The composition of the invention may take the form of a neat solution or liquid concentrate, dispersion, emulsion, aerosol, gel or solid. The invention may also take the form of a liquid impregnated sponge or towelette where the carrier comprises, in addition to a liquid, a chemically inert carrier such as a fabric or sponge. Accordingly, the choice of any carrier useful in the invention will depend somewhat on the intended form and intended use application of the final composition. If the invention takes the form of a solution, dispersion, emulsion, aerosol, gel, or solid useful carriers include water or aqueous systems as well as organic solvents and organic and inorganic based solid carriers. Preferably the organic solvent is of food grade purity and food additive classification as certified by the Food Chemicals Codex and United States Food and Drug Administration respectively.

Organics which have been found especially useful include simple alkyl alcohols such as ethanol, methanol, isopropanol, and the like. Also useful are polyhydric alcohols such as, glycerol, sorbitol, propylene glycol, polyethylene glycols, and the like. Any of these compounds may be used singly or in combination with other organics or water.

If the invention is formulated as a solid, the carrier may be selected from any organic or inorganic compound or mixture thereof which imparts a solid form and hardness to the present composition. These solids may be formed by a hot melt, pour-cast manufacturing process, extrusion or by compression. Typical organic ingredients which may be used in the antimicrobial composition of the invention to harden this composition include amides and polyols, as well as certain high melting point nonionic and anionic surfactants.

For example, stearic monoethanolamide, stearic diethanolamide and urea have been found to effectively result in the formation of a hardened product. In addition, carboxylic acids themselves can be used to harden solids or act as binders in compression solids forming. Moreover, polyols such as polyethylene glycol, and polyhydric sugar alcohols such as mannitol, and the like or mixtures thereof have all been found to impart a hardened but soluble character when combined in the composition of the invention.

Surfactants useful in the invention as a carrier are solid, generally high melting analogs of nonionics and anhydrous metallic salts of anionic surfactants. Liquid surfactants, both anionic and nonionic, may be used as carriers for liquid systems in accordance with the invention.

Preferred surfactants include nonyl phenol ethoxylates, linear alkyl alcohol ethoxylates, ethylene oxide-propylene oxide block copolymers, glycerol esters, polyoxyethylene glycerol esters, polyglycerol esters, sorbitan esters, polyoxyethylene sorbitan esters, sucrose esters, polyethylene ethers, dioctyl sodium sulfo succinate, stearoyl lactylate, and complex esters such as acetylated, lactylated, citrated, succinylated, and diacetyl tartarated glycerides.

Other organic compounds which may be used as hardeners within the composition of the invention include sugars, and modified starches or cellulosies which have been made water soluble through acid or alkaline treatment processes.

Inorganics which may be used in forming the hardened antimicrobial composition of the invention include salts formed of Periodic Groups IA and IIA metals; also including ammonium with the corresponding negative ions or radicals of mineral acids such as chloride ions, carbonate ions, nitrate ions, phosphate ions, sulfate ions, as well as their respective hydrates, protic salt forms, or in the case of phosphates, the various condensate species. Generally, any type of carrier capable of solidifying the antimicrobial agent may be used in accordance with the invention. However, preferably, the solidifying agent has food additive status as defined by the United States Food and Drug Administration. To this end, urea, Pluronic TM F-108 and polyethylene glycol have been found to be beneficial solidifying agents.

Generally, depending on whether the composition is a concentrate or use dilution formulation, the carrier comprises a significant portion of the composition of the invention ranging from about 50 wt-% or more to about 99.4 wt-%, preferably from about 60 wt-% to about 98.0 wt-%, and most preferably from about 70 wt-% to about 95 wt-%.

Notably, the carrier should be chosen and used at a concentration which does not inhibit the antimicrobial efficacy of the active in the present composition; and be preferably food additive.

III. Adjuvants

Alternatively, the composition of the invention may also comprise any number of adjuvants. Depending upon the formulatory benefits provided the composition, the adjuvants may partially or wholly displace any carrier used in the composition. Generally, in accordance with the invention, there may be included within this composition formulatory adjuvants or adjuvants which assist in the application of the invention with respect to performance, form, aesthetics and stability when stored or used within adverse conditions.

Formulatory adjuvants include coupling agents, solubilizers, or hydrotropes used to solubilize the antimicrobial agent of the invention; as well as maintain the storage stability of the present composition. This function may be accomplished exclusively by the carrier whether liquid or solid, organic or inorganic. However, in situations which require formulation of a concentrated antimicrobial system, an additional inorganic or organic agent may be introduced into the system to facilitate solubilization of the antimicrobial agent.

To this end, any number of organic coupling agents may be used including monofunctional and polyfunctional alcohols. Those coupling agents which have been found most useful include linear alkyl alcohols such as, for example, ethanol, isopropanol, and the like. Polyfunctional alcohols include glycerol, polyethylene glycol, propylene glycol, sorbitol and the like. Most preferably, any coupling agent used in the present composition has food additive status so as to ensure the safety of the composition if consumed.

The concentration of these compounds when used in this capacity generally, depending upon whether the composition is a concentrate or use dilution formulation, ranges from about 0 wt-% to about 80 wt-%, preferably from about 0 wt-% to about 60 wt-%, and most preferably from about 0 wt-% to about 55 wt-%.

In addition, acidulants may also be considered part of the adjuvant constituency. These may comprise one or more organic or inorganic acidulants useful in lowering the pH of the present composition. Acidulants useful in the present composition include all food grade and food additive organic and inorganic acids. Specific examples of said acidulants are; lactic acid, phosphoric acid, sulfuric acid, adipic acid, tartaric acid, succinic acid, acetic acid, propionic acid, fumaric acid, citric acid, malic acid, or mixtures thereof. Preferred acids include lactic acid and propionic acid. Propionic acid has been found to have advanced coupling effects in aqueous environments along with the ability to alter the pH of the composition. Further it has been found that concentrations of acid resulting in a use solution pH ranging from about 2 to 6.5, preferably from about 2.5 to 5.5, and most preferably from about 2.5 to 5.0 provide the most desirable antimicrobial efficacy.

The composition of the invention may also comprise anionic and nonionic surfactants (surface active agents). These may be used to solubilize constituents in the formulary process or provide storage stability of formulated product, as well as the use utility of providing cleaning capabilities (through lowering of surface tension coefficients) to the invention. Any number of surfactants or combination thereof may be used in accordance with the invention.

The surface active agents which have been found useful in accordance with the invention include anionic and nonionic agents including, for example, propylene glycol esters, glycerol esters, polyoxyethylene glycerol esters, polyglycerol esters, sorbitan esters, polyoxyethylene sorbitan esters, sucrose esters, polyethylene glycol esters, polyoxyethylene-polyoxypropylene ether adducts, dioctylsodium succinate, stearoyl lactylate, and complex esters such as acetylated or lactylated, citrated, succinylated, and diacetyl tartarated glycerides.

One class of surfactants which has been found especially useful in formulating various embodiments of the present composition includes nonionic surfactants which have a mixture of hydrophilic and hydrophobic character created by the presence of polyoxyethylene and polyoxypropylene moieties. Generally, nonionic surfactants which are especially useful include those surfactants having about 200 to 300 moles of ethoxylation and about 30 to 80 moles of propoxylation. Preferably, the nonionic surfactant has food additive status.

One surfactant which has been found most useful is Pluronic TM F-108 which is a nonionic surfactant generally defined as a polyoxyethylene, polyoxypropylene block copolymer sold by BASF-Wyandotte Company Inc.

Surface tension altering constituents of the invention may be used in the present composition, regardless of former application, in concentrations ranging from about 0 to 65 wt-%, preferably from about 0.01 wt-% to 55 wt-%, and most preferably from about 0.02 wt-% to 45 wt-%.

Here again, the concentration of surfactant adjuvant may vary depending upon the nature of the formulatory composition as a whole, the concentration of antimicrobial agent, as well as the nature of the storage and application environments among other factors.

The claimed composition may also take the form of an aqueous or organic spray. The spray may take the form of a pump spray or an aerosol spray. In instances where an aerosol spray is used, various aerosol propellants may be present including n-butane, isobutane, n-propane, and the like. Preferably, the aerosol will contain iso-butane which is cleared as food additive. The concentration for propellants may range from about 3 wt-% to about 25 wt-%, from about 4 wt-% to about 20 wt-%, and preferably from about 5 wt-% to about 15 wt-%.

The composition of the invention may also comprise adjuvants which facilitate the application of this composition to any number of environments through various vehicles. Specifically, the composition of the invention is useful as an antimicrobial agent in hand creams, sponges, towelettes, hand cleansers, personal care cleansers, dips, sprays and washes among other uses.

Accordingly, the composition of the invention may comprise any number of conditioners or emollients, humectants, perfumes, thickeners, opacifiers or particulates, colorants or dyes, cleansers or other agents useful in facilitating the application of the composition of the invention to its intended application.

Depending upon the physical form, the composition of the invention may be formed by methods known to those of skill in the art including compression molding, pour casting, and hot melt casting. The following table provides a general directory of concentrations for the various compositional forms of the invention.

| EMBODIMENT CONCENTRATION RANGES (wt-%) BY PRODUCT FORM | | | |
| --- | --- | --- | --- |
| | USEFUL | PREFERRED | MOST PREFERRED |
| USE SOLUTION | | | |
| Sorbic Acid | 0.1–3 | 0.1–1.5 | 0.2–0.7 |
| Benzoic Acid | 0.05–6 | 0.05–3 | 0.05–1.5 |
| Carrier | 50–99.85 | 60–99.85 | 70–99.75 |
| Adjuvants | 0–50 | 0–40 | 0.05–30 |
| Use Solution pH | 2–6.5 | 2.5–5.5 | 2.5–5.0 |
| LIQUID CONCENTRATE* | | | |
| Sorbic Acid | 1–15 | 1–12 | 1–10 |
| Benzoic Acid | 0.5–30 | 0.5–25 | 0.5–20 |
| Carrier | 40–98.5 | 50–98.5 | 60–98.5 |

| -continued EMBODIMENT CONCENTRATION RANGES (wt-%) BY PRODUCT FORM | | | |
|---|---|---|---|
| | USEFUL | PREFERRED | MOST PREFERRED |
| Adjuvants | 0–60 | 0–50 | 0–40 |

| SOLID CONCEN-TRATE* | USEFUL | PREFERRED | MOST PREFERRED |
|---|---|---|---|
| Sorbic Acid | 0.05–80 | 1–68 | 2–60 |
| Benzoic Acid | 0.1–80 | 0.5–70 | 1–60 |
| Carrier | 0–98.85 | 20–98.5 | 30–97 |
| Adjuvants | 0–99.85 | 0–98.5 | 0–97 |

*Use dilution pH of concentrates is substantially similar to ranges attained with Use Solution.

| PERSONAL CARE CLEANSERS GEL HAND SOAP | USEFUL | PREFERRED | MOST PREFERRED |
|---|---|---|---|
| Sorbic Acid | .05–3 | 0.1–1.5 | 0.1–0.7 |
| Benzoic Acid | .05–6 | 0.05–3.00 | 0.05–1.50 |
| Carrier | 30–99.9 | 35–99.85 | 40–99.85 |
| Adjuvants | 0–80 | 0.25–62.0 | 0.5–55 |
| Product pH | 2–6.5 | 2.5–5 | 2.5–5 |

Generally adjuvants such as surfactants, polyethylene glycol, mineral oil and the like may be present in a concentration ranging from about 0 wt-% to 80.0 wt-%, preferably from about 0 wt-% to 62.0 wt-%, and most preferably from about 0 to 55 wt-% when present.

WORKING EXAMPLES

Following below are formulatory, stability, application and microbiological working examples using the composition of the invention. While the invention is exemplified by the working examples, it is not limited to the examples shown hereinafter.

Working Example I

To be registered as a food contact sanitizer, a microbicide must provide a 5 log order reduction of the test organisms within 30 seconds, (Official Methods of Analysis of the Association of Official Analytical Chemists; Paragraph 960.09, 15th Ed., 1990). Table IA shows formulation of working and comparative examples used in bactericidal testing of the composition of the invention. The pH of the test solutions was adjusted to pH 2.6 to 3.0 with lactic acid in order to maintain a uniform pH for comparison.

TABLE IA

| | FORMULATIONS WT % | | | | | | | | | | |
|---|---|---|---|---|---|---|---|---|---|---|---|
| | WORKING EXAMPLES | | COMPARATIVE EXAMPLES | | | | | | | | |
| CONSTITUENT | 1A | 1B | 1A | 1B | 1C | 1D | 1E | 1F | 1G | 1H | 1I |
| Sorbic | 0.30 | 0.25 | 0.23 | 0.30 | 0.23 | 0.23 | 0.30 | 0.30 | 0.30 | 0.23 | |
| Benzoic | 0.30 | 0.25 | | | | | | | 0.30 | | |
| Propionic Acid | | | | 0.30 | | | | | | 0.23 | |
| Adipic Acid | | | | | 0.23 | | | | | | |
| Malic Acid | | | | | | 0.23 | | 0.30 | | | |
| Succinic Acid | | | | | | | 0.30 | | | | |
| Lactic Acid | 0.25 | 0.30 | 0.20 | 0.25 | 0.25 | 0.25 | 0.25 | 0.25 | 0.25 | 0.25 | 0.7 |
| Ethanol | 20.00 | 15.00 | 13.00 | 20.00 | 12.30 | 13.60 | 20.00 | 20.00 | 20.00 | 13.60 | 20.0 |
| Deionized Water | 79.15 | 84.20 | 86.34 | 79.15 | 86.99 | 85.69 | 79.15 | 79.15 | 79.15 | 85.69 | 79.3 |

TABLE IB

| ANTIMICROBIAL TESTING LOG REDUCTIONS | | |
|---|---|---|
| | Log Reduction (CFU/ml) | |
| COMPOSITION | S. aureus | E. coli |
| Working Example 1A | 6.85 | 6.97 |
| Working Example 1B | 3.59 | 5.00 |
| Comparative Example 1A | 2.58 | 1.60 |
| Comparative Example 1B | 1.30 | 1.10 |
| Comparative Example 1C | 1.44 | 1.07 |
| Comparative Example 1D | 2.92 | 1.04 |
| Comparative Example 1E | 1.05 | 1.02 |
| Comparative Example 1F | 0.82 | 0.98 |
| Comparative Example 1G | 0.53 | 0.82 |
| Comparative Example 1H | 2.55 | 0.79 |
| Comparative Example 1I | 1.97 | 0.72 |

The results of Table IB indicate the unique character of the microbicidal activity of the invention, embodied in Working Examples 1A and 1B, which provided a 5 log order reduction of both *Staphylococcus aureus* and *Escherichia coli* thereby providing sanitizing efficacy, meeting A.O.A.C. requirements.

Working Example II

Testing was then undertaken to determine the antimicrobial effectiveness of one embodiment of the invention at pH's ranging from 3.0 to 4.0. As seen in Table II, Control compositions A and B contained the indicated wt-% of ethanol with the balance being water. Working Examples 2A through 2L contained the indicated amount of organic acids and ethanol with the balance being water. The pH in all solutions was adjusted with lactic acid.

TABLE II

| | pH Spectrum of Antimicrobial Activity | | | | | | | |
|---|---|---|---|---|---|---|---|---|
| | Sorbic Acid | Benzoic Acid | Ethanol | pH 3.0 | | pH 3.5 | | pH 4.0 | |
| Composition | Conc. (wt-%) | Conc. (wt-%) | Conc. (wt-%) | S. aureus Log red. | E. coli Log red. | S. aureus Log red. | E. coli Log red. | S. aureus Log red. | E. coli Log red. |
| Control A | — | — | 15 | 1.09 | 0.38 | — | — | — | — |

TABLE II-continued

| | | | | pH Spectrum of Antimicrobial Activity | | | | | |
| | Sorbic Acid | Benzoic Acid | Ethanol | pH 3.0 | | pH 3.5 | | pH 4.0 | |
| Composition | Conc. (wt-%) | Conc. (wt-%) | Conc. (wt-%) | S. aureus Log red. | E. coli Log red. | S. aureus Log red. | E. coli Log red. | S. aureus Log red. | E. coli Log red. |
| --- | --- | --- | --- | --- | --- | --- | --- | --- | --- |
| Control B | — | — | 20 | 4.00 | 0.38 | 0.48 | 0.62 | 0.49 | 0.67 |
| 2A | 0.1 | — | 15 | 4.52 | 0.36 | — | — | — | — |
| 2B | 0.2 | — | 15 | 5.00 | 0.38 | — | — | — | — |
| 2C | 0.1 | — | 20 | 5.00 | 0.42 | 0.59 | 0.54 | 0.83 | 0.59 |
| 2D | 0.2 | — | 20 | 5.00 | 0.95 | 1.26 | 0.58 | 1.79 | 0.58 |
| 2E | 0.3 | — | 20 | 5.00 | 4.48 | 1.96 | 1.23 | 5.00 | 1.02 |
| 2F | — | 0.1 | 20 | 5.00 | 0.48 | 0.99 | 0.69 | 1.16 | 0.68 |
| 2G | — | 0.2 | 20 | 5.00 | 0.51 | 2.42 | 1.29 | 4.51 | 0.72 |
| 2H | — | 0.3 | 20 | 5.00 | 1.92 | 4.40 | 5.00 | 5.00 | 5.00 |
| 2I | 0.1 | 0.1 | 20 | 5.00 | 1.41 | 1.66 | 0.76 | 3.16 | 0.72 |
| 2J | 0.15 | 0.15 | 20 | — | — | 3.47 | 3.85 | 5.00 | 1.88 |
| 2K | 0.2 | 0.2 | 20 | 5.00 | 5.00 | 5.00 | 5.00 | 5.00 | 5.00 |
| 2L | 0.25 | 0.25 | 20 | 5.00 | 5.00 | 5.00 | 5.00 | 5.00 | 5.00 |

The data in Table II indicate that both sorbic acid (Working Examples 2A-2E) and benzoic acid (Working Examples 2F-2H) alone are effective against Staphylococcus aureus at pH 3.0. However, neither sorbic acid, nor benzoic acid alone are totally effective against Escherichia coli at pH 3.

At pH 3.5 the effectiveness on an overall basis appeared to drop somewhat except that the relative effectiveness of Working Examples 2I through 2L appeared to be unaffected.

At pH 4.0 the effectiveness of all compositions appears to have improved on the whole. Working Examples 2K and 2L maintained their activity of 5 log order kill at all three pH levels.

Working Example III

Wide microbiocidal spectrum is a very important characteristic in selecting a sanitizer or disinfectant for treating food handling or processing equipment. This spectrum may include microorganisms responsible for food borne illnesses, such as Staphylococcus aureus and Salmonella choleraesuis; food spoilage microorganism, such as Aspergillus niger and Saccharomyces cerevisiae; and pathogenic microorganisms, such as Trichophyton mentagrophytes, Candida albicans and Staphylococcus aureus, Pseudomonas aeruginosa and sometimes Escherichia coli. The pathogenic organisms are also important in health ,care facilities, day-care centers and the like, where it is important to control the spread of pathogens directly and indirectly from person to person.

The compositions shown in Table IIIA were prepared by mixing the constituents together for thirty minutes and then adjusting the pH. Both the sanitizing and disinfecting tests were performed in accordance with A.O.A.C. testing.

TABLE IIIA

| | FORMULATIONS (wt-%) | | |
| CONSTITUENT | WORKING EXAMPLE 3 | COMPARATIVE EXAMPLE 3A | COMPARATIVE EXAMPLE 3B |
| --- | --- | --- | --- |
| ETHANOL | 22.00 | 22.00 | 14.00 |
| SORBIC ACID | 0.40 | — | — |
| BENZOIC ACID | 0.20 | — | — |
| LACTIC ACID | 0.15 | 0.15 | 0.50 |
| PLURONIC F108 | 0.03 | 0.03 | — |
| WATER | 77.22 | 77.82 | 85.06 |
| PHOSPHORIC ACID | — | — | 0.44 |
| final pH | 2.86 | 2.80 (lactic acid) adj. | 2.85 (KOH adj.) |

TABLE IIIB

ANTIMICROBIAL TESTING

| | SANITIZING EFFICACY (LOG REDUCTION (CFU/ml))* | | |
| | WORKING EXAMPLE | COMPARATIVE EXAMPLES | |
| | 3 | 3A | 3B |
| --- | --- | --- | --- |
| E. coli | 5.00 | 0.47 | 0.51 |
| S. aureus | 5.00 | 0.41 | 1.28 |
| DISINFECTING EFFICACY (no growth tubes/total tubes) A.O. A. C. USE DILUTION TEST | | | |
| W/O SERUM | | | |
| S. aureus | 60/60 | 0/20 | 17/20 |
| S. choleraesuis | 59/60 | 20/20 | 19/20 |
| P. aeruginosa | 60/60 | 20/20 | 19/20 |
| WITH SERUM | | | |
| S. aureus | 60/60 | 1/20 | 4/20 |
| S. choleraesuis | 59/60 | 19/20 | 20/20 |
| P. aeruginosa | 60/60 | 20/20 | 16/20 |
| FUNGICIDAL | | | |
| T. mentagrophytes | 20/20 | 0/20 | 0/20 |
| A. Niger | 20/20 | 0/20 | 0/20 |
| YEAST | | | |
| C. albicans | 20/20 | 0/20 | 0/20 |
| S. cerevisae | 20/20 | 0/20 | 0/20 |

*Colony Forming Units Per Milliter

The data in Table IIIB demonstrates that comparative examples 3A and 3B containing ethanol, lactic acid and phosphoric acid are not active against the fungi and yeast species. Likewise, Comparative Examples 3A and 3B were somewhat effective against the Salmonella choleraesuis and Pseudomonas aeruginosa in the disinfectant testing, but not active in the sanitizing testing.

Meanwhile, Working Example 3 was unconditionally effective in all of the tests and demonstrates a wide microbiocidal spectrum.

Working Example IV

The composition of the invention may also be incorporated into a sanitizing wipe. The composition of the invention may be altered depending on whether it is to be used for sanitizing handwipes or hard surface sanitizing wipes. In the case of hand sanitizing towelettes, humectants may be added to provide an improved hand feel. These may include glycerol, propylene glycol, sorbitol, and the like.

Incorporating an antimicrobial into a presaturated sanitizing or disinfectant wipe offers the advantage that it can be disposed of when soiled without worry of spreading microbial contamination. The composition of the invention is compatible with natural and synthetic fibers including cellulosic, polyester, polypropylene, or blends (cotton-polyester) of woven or non-woven fabrics.

In the formulation of embodiments of the invention useful in towelette form, Working Examples 4A through 4F were formulated by mixing the relative amounts of constituents for a time adequate to provide uniform solutions. Towelettes of non-woven fabric were then saturated with the respective solutions. These compositions were then stored without detriment to their relative antimicrobial efficacy.

TABLE IV

| Ingredients wt % | 4A | 4B | 4C | 4D | 4E | 4F |
|---|---|---|---|---|---|---|
| Sorbic Acid | 0.20 | 0.30 | 0.40 | 0.30 | 0.40 | 0.4 |
| Benzoic Acid | 0.10 | 0.10 | 0.20 | 0.10 | 0.20 | 0.2 |
| Ethanol | 12.00 | 20.00 | 22.00 | 18.00 | 22.00 | 22.0 |
| Pluronic F108 | — | 0.30 | 0.30 | — | — | — |
| Propylene Glycol | — | — | — | 10.00 | 5.00 | 5.0 |
| Glycerine | — | — | — | 3.00 | — | 3.0 |
| Lactic Acid | 0.15 | 0.15 | 0.15 | 0.30 | 0.15 | 0.2 |
| Deionized Water | qs | qs | qs | qs | qs | qs |
| pH adjusted 2.8–4.0 | | | | | | |

The compositions of Working Examples 4A through 4C are appropriate for use as a hard surface cleaner disinfectant wipe. The composition of Working Examples 4D through 4F are appropriate for human or animal use as sanitizing dips, wipes or cloths.

Working Example V

The composition of the invention may be incorporated into a hand cream base to provide antimicrobial properties, with aesthetic appeal. The following table discloses two exemplary hand cream formulas (5A and 5B) which may use the composition of the invention.

| Ingredients (wt-%) | Example 5A | Example 5B |
|---|---|---|
| Part A | | |
| Sorbic Acid | 0.2 | 0.4 |
| Benzoic Acid | 0.1 | 0.2 |
| Ethanol | 5.0 | 15.8 |
| Propylene Glycol | 5.0 | 5.0 |
| Glycerol | 3.0 | 3.0 |
| Lactic Acid (for pH adj.) | qs | qs |
| Deionized Water | 65.7 | 57.6 |
| pH adjusted to 2.8–4.0 | | |
| Part B | | |
| Glycerol Stearate | 8.0 | 8.0 |
| Glycerol Stearate/PEG 100 | 5.0 | 3.0 |
| Mineral Oil | 6.0 | 3.0 |
| Bees Wax | 1.0 | 3.0 |
| Pluronic F108 | 1.0 | 1.0 |

This product is formed by standard two part emulsion mix. Part A is mixed until homogeneous and pH adjusted to 2.8–4.0.

Part B is weighed, heated to 60° C. with agitation until all ingredients are melted and homogeneous. Thereafter, Part A is heated to 50° C. and Part A is added to Part B under high sheer mixing until a homogeneous, white, smooth product is formed and cooled to 30° C. These formulas exhibited long shelf stability.

Working Example VI

Sanitizing hand soaps control food borne illnesses such as pathogenic bacteria which may be transferred from the food handler to the product as well as those bacteria which are transferred in cross contamination of food stuffs. In this classification, the U.S. Department of Agriculture has designated sanitizing hand soaps which may be used before returning to work in food process areas as E2 hand sanitizing cleansers.

Typically, active ingredients which meet antimicrobial requirements in this type of soap such as chlorine, iodine, parachlorometaxylenol and chlorohexidine gluconate are deleterious to the skin.

The composition of the invention may be incorporated into an hand sanitizing soap to provide a product which exhibits the antimicrobial activity necessary to pass the required U.S.D.A. test protocol. Chlorine Germicidal Equivalency Concentration; Method 955.16, A.O.A.C. Official Methods of Analysis, 15th Edition, Vol. 1, 1990.

The composition of the invention is compatible with a wide variety of surfactants, providing a measure of latitude in formulation. Table VIA illustrates four formulations useful as hand soaps which incorporate the composition of the invention.

TABLE VIA

SANITIZING HAND SOAP FORMULAS

| FORMULA | wt % 6A | 6B | 6C | 6D |
|---|---|---|---|---|
| Sorbic Acid | 0.2 | 0.2 | 0.2 | 0.4 |
| Benzoic Acid | 0.1 | 0.1 | 0.1 | 0.2 |
| Ethanol | 8.0 | 8.0 | 8.0 | 15.0 |
| Propylene Glycol | 5.0 | 5.0 | 5.0 | — |
| Glycerine | — | 3.0 | — | 3.0 |
| Sorbitol | 6.0 | — | 5.0 | 5.0 |
| Sodium Lauryl Sulfate | — | 20.0 | — | — |
| Sodium Lauryl Ether Sulfate | 15.0 | — | — | 12.0 |
| Sodium Alpha Olefin Sulphonate | — | — | 22.0 | — |
| Triethanolamine linear alkane sulphonate | — | — | — | 3.0 |
| Sodium Laureth Sulfosuccinate | 6.0 | 12.0 | — | 4.0 |
| Hydroxypropyl Guar | — | — | — | 0.4 |
| Hydroxyethyl Cellulose | 0.5 | 0.5 | 0.5 | — |
| Lactic Acid | 3.0 | 3.0 | 4.0 | 4.0 |
| Deionized Water | 56.2 | 48.2 | 55.2 | 53.0 |
| pH 3.5–4.5 adjusted with Lactic Acid | | | | |

TABLE VIB

Antimicrobial Results
CHLORINE GERMICIDAL EQUIVALENCY TEST

| Sample | PPM | 1 | 2 | 3 | 4 | 5 | 6 | 7 | 8 | 9 | 10 |
|---|---|---|---|---|---|---|---|---|---|---|---|
| *Staphylococcus aureus* Subculture Series | | | | | | | | | | | |
| Chlorine | 50 | − | − | − | + | + | + | + | + | + | + |
| Chlorine | 100 | − | − | − | − | − | + | + | + | + | + |
| Chlorine | 200 | − | − | − | − | − | − | − | − | + | + |
| Formula 6B | 1:1 | − | − | − | − | − | − | − | − | − | − |
| *Salmonella typhi* Subculture Series | | | | | | | | | | | |
| Chlorine | 50 | − | − | − | + | + | + | + | + | + | + |
| Chlorine | 100 | − | − | − | − | − | + | + | + | + | + |
| Chlorine | 200 | − | − | − | − | − | − | − | − | + | + |
| Formula 6B | 1:1 | − | − | − | − | − | − | − | − | − | − |

Key
− indicates no growth
+ indicates growth

Table VIB illustrates this antimicrobial data. The Working Example 6B was diluted 1:1 with deionized water, then tests run. As can be seen, Working Examples 6B exhibits antimicrobial efficacy greater than 200 ppm available chlorine equivalents.

Working Example VII

The invention may also be formulated in the form of a concentrate. In turn, these may then be used as dilutions to form use concentration disinfectant or sanitizing solutions as needed. Tables VIIA and VIIB provide compositional formulations and dilution schemes for compositions in accordance with the invention.

TABLE VIIA

| | (WT-%) | | | |
|---|---|---|---|---|
| CONSTITUENT | 7A | 7B | 7C | 7D |
| ETHANOL | 50.0 | 73.05 | 96.2 | 97.16 |
| SORBIC ACID | 1.0 | 1.50 | 1.5 | 1.76 |
| BENZOIC ACID | 0.5 | 0.75 | 1.5 | 0.88 |
| PROPYLENE GLYCOL | 10.0 | 15.00 | — | — |
| LACTIC ACID | 1.5 | 2.00 | 0.8 | — |
| PHOSPHORIC ACID | — | — | — | 0.20 |
| WATER | q.s | q.s. | — | — |

These were then diluted in water to yield use solutions in the following manner.

TABLE VIIB

| Working Example | Dilution |
|---|---|
| 7A | 1 part Working Example 7A in total of 2.5 parts solution |
| 7B | 1 part Working Example 7B in total of 3.75 parts solution |
| 7C | 1 part Working Example 7C in total of 5.00 parts solution |
| 7D | 1 part Working Example 7D in total of 4.40 parts solution |

Working Example VIII

An additional embodiment of the invention was then formulated based solely on an aqueous carrier. Generally, the antimicrobial agent of the invention, in its most preferred form, as sorbic acid and benzoic acid was intermixed with water in the concentrations provided in Table VIIIA. The pH of this system without adjustment ranged from 2.9 to 3.0. This pH was adjusted higher with potassium hydroxide to investigate the solubility profile of the compositions as well as the effective antimicrobial properties of this composition. Additionally, we discovered that the use of propionic acid provided a highly soluble system having high antimicrobial efficacy. The antimicrobial efficacy of these compositions is tested as indicated in Table VIIIB. As can be seen, all samples measured at 40° C. had a high sanitizing efficacy. Furthermore, those samples measured at 25° C. having a pH below 3.0 also had a high efficacy.

TABLE VIIIA

| CONSTITUENTS (wt-%) | 8A | 8B | 8C | 8D | 8E |
|---|---|---|---|---|---|
| Sorbic acid | 0.4 | 0.4 | 0.4 | 0.4 | 0.4 |
| Benzoic acid | 0.2 | 0.2 | 0.2 | 0.2 | 0.2 |
| Propionic acid | — | — | 5.0 | 15.0 | 15.0 |
| H₂O | 99.4 | 99.4 | 94.4 | 84.4 | 84.4 |
| pH (Adjusted with 45% KOH) | 3.0 | 3.5 | 3.5 | 2.3 | 2.9 |

TABLE VIIIB

SANITIZING EFFICACY

| | | | Log Reductions (CFU/mL) | |
|---|---|---|---|---|
| Formula | pH | test temp (°C.) | E. coli | S. aureus |
| 8A | 3.0 | 40 | 7 | 7 |
| 8B | 3.5 | 40 | 7 | 4.85 |
| 8A | 3.0 | 25 | <1 | <1 |
| 8B | 3.5 | 25 | <1 | <1 |
| 8C | 3.5 | 40 | 7 | 7 |
| 8C | 2.3 | 25 | 7 | 7 |
| 8D | 2.9 | 25 | 7 | 7 |

Working Example IX

This invention may also take the form of a solid concentrate. This solid may be formed by cast melt pour, extrusion or compression. The specific manufacturing method should be dictated by the required product properties and raw materials to achieve these. The following examples were dry blended and compression formed to effect a rigid non-friable tablet.

TABLE IX

| | Working Examples (wt-%) | | | | | | | | |
|---|---|---|---|---|---|---|---|---|---|
| Constituents | A | B | C | D | E | F | G | H | I |
| Sorbic Acid | 66.6 | 40 | 30 | 40 | 40 | 4 | 40 | 4 | 20 |
| Benzoic Acid | 33.4 | 20 | 15 | 20 | 20 | 2 | 20 | 2 | 10 |
| Dextrose Powder | — | — | 25 | — | 40 | 94 | — | — | — |
| Mono Sodium Phosphate | — | — | — | 40 | — | — | — | — | 10 |
| Polyethylene Glycol 8000 MW | — | — | — | — | — | — | 40 | 10 | — |
| Citric Acid | — | 40 | 30 | — | — | — | — | 84 | — |
| Pluronic ™ F-108 | — | — | — | — | — | — | — | — | 60 |

The above specification, examples and data provide a complete description of the manufacture and use of the composition of the invention. Since many embodiments o#the invention can be made without departing from the spirit and scope of the invention, the invention resides in the claims hereinafter appended.

We claim as our invention:

1. A method of sanitizing hard surfaces with an aqueous sanitizing composition, said method comprising:
   (a) diluting with an aqueous carrier an antimicrobial composition consisting essentially of:
   (i) from about 0.05 wt % to 80 wt % of sorbic acid, a sorbic acid salt or mixtures thereof;
   (ii) from about 0.05 wt % to 80 wt % of benzoic acid, a benzoic acid salt or mixtures thereof;
   (iii) a solubilizing amount of a $C_1$–$C_6$ alcohol; and
   (iv) an amount of acidulant to maintain the pH between about 2.0 to 6.5, to obtain from about 0.05 wt % to about 3 wt % sorbic acid, a sorbic acid salt, or mixtures thereof, and about 0.05 wt % to about 6 wt % of benzoic acid, a benzoic acid salt, or mixtures thereof; and
(b) applying said diluted sanitizing composition to a surface for a sufficient period of time to result in a 5 $\log_{10}$ reduction in a microbial population on the surface.

* * * * *

UNITED STATES PATENT AND TRADEMARK OFFICE
CERTIFICATE OF CORRECTION

PATENT NO. : 5,336,500

DATED : August 9, 1994

INVENTOR(S) : Francis L. Richter et al.

It is certified that error appears in the above-identified patent and that said Letters Patent is hereby corrected as shown below:

On column 6, line 10, please delete "impeded" and substitute therefore --impede--

On column 7, line 23, please delete "comprises" and substitute therefore --comprise--

On column 12, line 7, please delete "0.30" under "1G"

On column 12, line 8, please insert --Tartaric-- under "Constituent" column

On column 12, line 8, please insert --0.23-- under "2nd 1A"

On column 12, line 8, please insert --0.30-- under "1G"

On column 13, line 46, please delete "," after the word "health"

On column 14, line 42 (last line under table), please delete "Milliter" and substitute therefore --Milliliter--

On column 16, line 35, please delete "an" and substitute therefore --a--

UNITED STATES PATENT AND TRADEMARK OFFICE
CERTIFICATE OF CORRECTION

PATENT NO. : 5,336,500
DATED : August 9, 1994
INVENTOR(S) : Francis L. Richter, et. al.

It is certified that error appears in the above-indentified patent and that said Letters Patent is hereby corrected as shown below:

On column 18, line 54, please delete "o#" and substitute therefore --of--.

Signed and Sealed this

Twenty-second Day of November, 1994

Attest:

BRUCE LEHMAN

*Attesting Officer*  *Commissioner of Patents and Trademarks*